(12) United States Patent
Buckland et al.

(10) Patent No.: US 9,869,659 B2
(45) Date of Patent: Jan. 16, 2018

(54) ACOUSTIC SENSOR

(71) Applicant: THE TECHNOLOGY PARTNERSHIP PLC., Royston, Hertfordshire (GB)

(72) Inventors: Justin Rorke Buckland, Cambridge (GB); Andrew Robert Campbell, Cambridge (GB)

(73) Assignee: The Technology Partnership PLC. (GB)

( * ) Notice: Subject to any disclaimer, the term of this patent is extended or adjusted under 35 U.S.C. 154(b) by 677 days.

(21) Appl. No.: 14/363,324

(22) PCT Filed: Dec. 6, 2012

(86) PCT No.: PCT/GB2012/053028
§ 371 (c)(1),
(2) Date: Jun. 6, 2014

(87) PCT Pub. No.: WO2013/083978
PCT Pub. Date: Jun. 13, 2013

(65) Prior Publication Data
US 2014/0338423 A1 Nov. 20, 2014

(30) Foreign Application Priority Data

Dec. 6, 2011 (GB) .................................. 1120887.3

(51) Int. Cl.
*G01N 29/02* (2006.01)
*G01N 29/036* (2006.01)
(Continued)

(52) U.S. Cl.
CPC ........... *G01N 29/02* (2013.01); *G01N 29/022* (2013.01); *G01N 29/036* (2013.01); *G01N 29/222* (2013.01); *G01N 33/0004* (2013.01)

(58) Field of Classification Search
CPC .... G01N 29/02; G01N 29/022; G01N 29/036; G01N 29/222; G01N 2291/014;
(Continued)

(56) References Cited

U.S. PATENT DOCUMENTS

| | | |
|---|---|---|
| 3,807,222 A | 4/1974 | Eggers |
| 3,848,457 A | 11/1974 | Behymer |

(Continued)

FOREIGN PATENT DOCUMENTS

| | | |
|---|---|---|
| EP | 0813060 A2 | 12/1997 |
| WO | 2006111775 A1 | 10/2006 |

(Continued)

OTHER PUBLICATIONS

Pethrick, "The Swept Frequency Acoustic Resonant Interferometer: Measurement of Acoustic Dispersion Parameters in the Low Megahertz Frequency Range" Journal of Physics E; Scientific Instruments, vol. 5, No. 6, Jun. 1972, pp. 571-574.
(Continued)

*Primary Examiner* — Laura Martin
*Assistant Examiner* — Rose M Miller
(74) *Attorney, Agent, or Firm* — Tarolli, Sundheim, Covell & Tummino LLP

(57) ABSTRACT

An acoustic sensor includes a side wall, closed at each end by an end wall, to form a substantially cylindrical cavity, a transmitter and a receiver operatively associated with first and second respective end walls. Properties of the relative dimensions of the cavity are configured to create a desired oscillatory motion of the end walls, and oscillations of a fluid pressure in the cavity, to generate an electrical signal via the receiver to be output from the sensor. An array of acoustic sensors can be connected to allow calibration of one of the array of sensors.

18 Claims, 7 Drawing Sheets

(51) Int. Cl.
*G01N 29/22* (2006.01)
*G01N 33/00* (2006.01)

(58) Field of Classification Search
CPC ..... G01N 2291/021; G01N 2291/0212; G01N 2291/0215; G01N 29/0217; G01N 2291/022; G01N 2291/0222; G01N 2291/0224; G01N 29/0226; G01N 2291/0228; G01N 2291/02408; G01N 29/02416
USPC ....... 73/649, 579, 32 A, 54.41, 61.45, 61.49, 73/61.75, 64.43, 64.53, 24.01, 24.03, 73/24.06, 31.05
See application file for complete search history.

(56) References Cited

U.S. PATENT DOCUMENTS

| | | | |
|---|---|---|---|
| 5,060,506 A | 10/1991 | Douglas | |
| 5,627,323 A | 5/1997 | Stern | |
| 5,804,698 A | 9/1998 | Belonenko et al. | |
| 5,836,200 A * | 11/1998 | Belonenko | G01L 9/0022 73/24.06 |
| 6,378,372 B1 | 4/2002 | Karr | |
| 6,490,911 B1 * | 12/2002 | Namerikawa | G01L 9/008 310/324 |
| 2005/0210956 A1 * | 9/2005 | Crane | G01N 29/036 73/24.01 |
| 2008/0028861 A1 | 2/2008 | Funck | |
| 2011/0023582 A1 * | 2/2011 | Kupnik | G01N 5/02 73/31.01 |

FOREIGN PATENT DOCUMENTS

| | | |
|---|---|---|
| WO | 2009112866 A1 | 9/2009 |
| WO | 2010139916 A1 | 12/2010 |
| WO | 2010139918 A1 | 12/2010 |

OTHER PUBLICATIONS

Eggers and Funck, "Ultrasonic Measurements with Milliliter Liquid Samples in the 05.-100 MHz Range" Rev. Sci. Instrum., vol. 44, No. 8, Aug. 1973, pp. 969-977.

Dong, Bai, Li and Viehland, Sound-Resonance Hydrogen Sensor Applied Physics Letters, vol. 82, No. 25, Jun. 2003, pp. 4590-4592.

* cited by examiner

ACOUSTIC SENSOR

BACKGROUND OF THE INVENTION

Field of the Invention

This invention relates to a resonant acoustic sensor, and in particular, to an acoustic sensor having a substantially disc shaped acoustic cavity with substantially circular end walls.

Description of Related Art

Devices which determine the composition of a gas mixture by measuring the speed of sound in that mixture are well known in the prior art. The two most prevalent acoustic techniques are the time-of-flight technique and the resonant cavity technique. The drawbacks and limitations of each type of device have been described in the prior art (EP 0813060) and will be summarised again here.

A time-of-flight device (for example: U.S. Pat. No. 5,060,506 and U.S. Pat. No. 5,627,323) uses a pair of transducers to transmit and receive short (typically on the order of microseconds) pulses of acoustic energy. The speed of sound is determined by measuring the time taken for these pulses to travel a known distance through the test fluid. In the devices referenced above, the composition of a binary gas mixture is determined from this measurement. Typical problems with such devices include signal attenuation, echoes, dimensional stability, poor temperature compensation, parasitic conduction, and poor pulse shaping and pulse shape distortion. These problems limit both the performance and long-term stability of time-of-flight devices.

Resonant cavity devices (for example: U.S. Pat. No. 3,848,457, EP 0813060, and U.S. Pat. No. 6,378,372) measure the resonant frequency of an acoustic cavity. When the acoustic cavity is filled with a fluid, the resonant frequency of the cavity directly relates to the composition of the fluid. A key limitation of the devices described in the prior art is the difficulty of efficiently exciting a single dominant mode of resonance in the cavity. Many competing resonant modes may exist within the sensor including radial, axial, longitudinal and azimuthal modes. This complicates the interpretation of the output of the sensor. Poor coupling between the, typically longitudinal, motion of the transmitting transducer (transmitter) into the resonant mode of the cavity, and poor coupling between the resonant mode of the cavity and the receiving transducer (receiver) produces a weak signal. Sources of electrical noise in the receiver such as parasitic signals passing from the transmitter to the receiver through the structure of the device, or mechanical resonance of components such as the diaphragm can be of a magnitude comparable to the signal itself.

The shortcomings of the above resonant sensors are shared by devices based upon a Helmholtz oscillator, for example the prior art disclosed in Appl. Phys. Lett., Vol. 82, No 25, Page 4590. In such a device the air in the neck of the aperture of a cavity vibrates causing pressure oscillations in that cavity which oppose the motion of the air in the neck, leading to simple harmonic motion. In the embodiment described by the above publication, the change in acoustic intensity resultant from changing density and speed of sound of the fluid in the cavity is used to measure the composition of a mixture of hydrogen and air. This design has the additional disadvantage that the single aperture in the resonant cavity prevents a flow of fluid from passing through the sensor cavity, which is desirable for fast response times and ease of integration into a fluidic system.

Given the shortcomings of time-of-flight and existing resonant cavity speed-of-sound sensors, there is a need for speed-of-sound sensor capable of efficiently generating a resonant oscillation significantly larger than competing resonant modes and parasitic oscillations. The efficient generation of a large amplitude radial mode pressure oscillation at the resonant frequency of the cavity overcomes many of the limitations of the prior art.

The efficient generation of resonant acoustic standing waves has been addressed in the field of fluid pumping. Patent applications WO2006/111775, WO2009/112866, WO2010/139916, and WO2010/139918 disclose pumps having substantially disc shaped cavities with high aspect ratios (i.e. the ratio of the radius of the cavity to the height of the cavity) which in operation generate a resonant acoustic standing wave in those cavities.

The pump disclosed in FIG. 1 of WO2006/111775 has a substantially cylindrical cavity 11 comprising a side wall 14 closed at each end by end walls 12, 13. The pump also comprises an actuator 20 that drives one or both of the end walls to oscillate in a direction substantially perpendicular to the surface of the plane of the end walls, referred to hereinafter as "axial oscillations". In this geometry, the mechanical stiffness of the actuator is well matched to the acoustic impedance of the cavity, enabling efficient generation of a high amplitude pressure oscillation.

The efficient generation of a pressure oscillation in such a cavity is further dependent on the matching of the spatial profile of the fluid oscillation in the cavity and the motion of the driven end wall. When the spatial profiles are well matched, work done by the actuator on the fluid in the cavity adds constructively, thereby enhancing the amplitude of the pressure oscillation in the cavity and delivering improved pump efficiency, referred to herein as mode-shape matching. Conversely, in a pump where the spatial profiles are poorly matched, work done by some regions of the end wall on the fluid reduces rather than enhances the amplitude of the fluid pressure oscillation in the fluid within the cavity. Thus, the useful work done by the actuator on the fluid is reduced and the pump becomes less efficient.

The above concepts are applied here to the design of a resonant acoustic sensor where both the transmitter (which is driven) and the receiver (which is passive) are operatively associated with opposing end walls of a disc shaped cavity. As a result of this geometry, in operation both the mechanical stiffness of the transmitter and the receiver of such a device are well matched to the acoustic impedance of the disc shaped volume of fluid in the cavity. This disc shaped geometry is also suitable for achieving good spatial matching between the displacement profiles of the transmitter and receiver and the radial fluid pressure oscillation in the cavity. The combination of these properties enables efficient generation of a high amplitude pressure oscillations by the transmitter and efficient generation of an output signal from the receiver, overcoming many of the limitations of the prior art.

SUMMARY

In the present invention a resonant acoustic sensor is designed with a substantially disc shaped acoustic cavity with substantially circular end walls. A transducer, herein known as the transmitter, is operatively associated with one of the end walls to cause an oscillatory motion of the associated end wall whereby, in use, these axial oscillations of the end wall drive radial oscillations of the fluid pressure in the cavity. The radial pressure oscillation in the cavity generates axial motion of the second end wall which is operatively associated with a second transducer, herein known as the receiver, which in turn generates an oscillatory electrical signal. By comparing the signal used to drive the transmitter to the signal generated by the receiver, properties of the fluid in the acoustic cavity can be determined.

According to the present invention there is provided an acoustic sensor comprising:
- a side wall closed at each end by an end wall to form a substantially cylindrical cavity which, in use, contains a fluid;
- a transmitter operatively associated with a first of the end walls;
- a receiver operatively associated with a second of the end walls;
- wherein a radius, a, of the cavity and a height, h, of the cavity satisfies the following inequality:

$$\frac{a}{h}$$

is greater than 1.2; and
- wherein, in use, the transmitter causes oscillatory motion of the first end wall in a direction substantially perpendicular to the plane of the end walls;
- such that the axial oscillations of the end wall drive substantially radial oscillations of the fluid pressure in the cavity; and
- the substantially radial oscillations in the pressure of the fluid drive oscillatory motion of the end wall associated with the receiver, generating an electrical signal.

To avoid excessive damping due to fluid viscosity the ratio $$\frac{h^2}{a}$$

may be greater than $4 \times 10^{-10}$ m. In the case where the fluid in the cavity is a gas, the ratio $$\frac{h^2}{a}$$

may be greater than $1 \times 10^{-7}$ m. The lowest resonant frequency of radial pressure oscillations achieved in the cavity in operation or in use may be greater than 20 kHz so that the device is inaudible to humans.

In use, the axial oscillations of the first end wall may drive a higher order radial mode of pressure oscillation in the cavity.

The end wall motion may be mode-shape matched to the pressure oscillation in the cavity and may additionally or alternatively approximate the form of a Bessel function. The transmitter or receiver may be a piezoelectric device, and may be formed of any electrically active or electromagnetically active material such as, for example, an electrostrictive or magnetostrictive material. The transmitter or receiver may include a flexible membrane.

The means for detecting a resonant oscillation in the fluid pressure of the cavity may include means for measuring the amplitude of the electrical signal from the receiver with respect to the amplitude of the electrical signal used to drive the transmitter. The means for detecting a resonant oscillation in the fluid pressure of the cavity may include means for measuring the phase of the electrical signal from the receiver with respect to the electrical signal used to drive the transmitter.

The acoustic sensor may be arranged such that the resonances of the transmitter and the receiver do not significantly overlap with the resonance of the cavity. Preferably the resonant frequency of the cavity and the resonant frequency of the transmitter and the receiver is described by the expression:

$$\left( f_{cavity} + \frac{f_{cavity}}{Q_{cavity}} \right) < \left( f_{transducer} - \frac{f_{transducer}}{Q_{transducer}} \right). \quad \text{[Eqn. 1]}$$

Where $f_{cavity}$ is the resonant frequency of the cavity, $Q_{cavity}$ is the quality factor of that resonance, $f_{transducer}$ is the resonant frequency of either the transmitter or the receiver and $Q_{transducer}$ is the quality factor of that resonance. The invention may further provide a sensor array comprising two or more acoustic sensors, wherein at least two sensor cavities are separated by a common end wall. One or more of the sensors may be arranged to allow calibration of one or more of the other sensors for factors including temperature, fluid pressure, thermal expansion or mechanical drift. At least one of the sensors may be enclosed in a casing. A fluid inlet to the casing may be manifolded to the fluid inlet of the sensor and the fluid outlet of the sensor may output fluid into the volume between the sensor and the casing.

The sensor or array may further comprise a temperature sensor operatively associated with the side walls and or end walls of the cavity. The sensor or array may further comprise a conduit through the material of the end side wall or one or more of the end walls of the sensor wherein, in use, the fluid flows through that conduit into the cavity. A heater may be operatively associated to the side walls and or end walls of the cavity. A side wall or one or more of the end wall(s) may be made from a material with thermal conductivity greater than 50 $Wm^{-1}K^{-1}$.

DETAILED DESCRIPTION OF ILLUSTRATIVE EMBODIMENTS

Figure 1A:
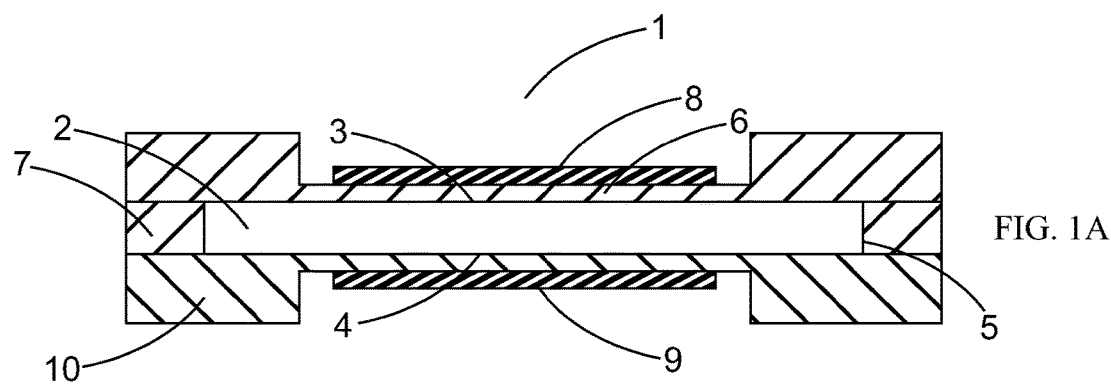
FIG. 1 shows a schematic cross section of an embodiment of the acoustic sensor, the displacement profile of the first end wall of the sensor, a graph of the pressure oscillations within the cavity of the sensor and the displacement profile of the second end wall of the sensor.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

FIG. 1 shows a schematic representation of an acoustic sensor 1 according to the present invention. A cavity 2 is defined by end walls 3 and 4, and a side wall 5. The cavity 2 is substantially circular in cross section as drawn, but other suitable shapes such as elliptical could be used. As with the pump disclosed in WO2006/111755, the present invention may be described as possessing a substantially disc shaped cavity. Cylindrical cavities are believed to provide optimised performance in the present invention. However, cavities having a non-circular cross-section can also be effective to some degree. As such, a substantially cylindrical cavity defined herein with respect to the present invention can encompass cavities having non-circular cross-sections and/or non-parallel walls, as well as cavities having frustro-conical end walls, or cavities having cross-sections which vary between the two end-walls. Although expressed for cylindrical forms, the properties and ratios described herein may be applied to either an average or maximum height or radius of a cavity where varying and/or non-circular cross sections of a cavity are used. In operation the sensor generates radial acoustic pressure oscillations. In particular, when the cavity radius a is greater than 1.2 times the height h of the cavity, i.e.

$$\frac{a}{h} > 1.2,$$

the lowest frequency radial mode of oscillation of the fluid in the cavity has a lower frequency than any longitudinal modes of the cavity. In operation it is preferable that the lowest frequency radial mode is at a frequency of 20 kHz or higher so that the device is inaudible in operation. A frequency of approximately 20 kHz or higher provides operation above the threshold of normal human hearing.

To avoid inefficient operation resultant from high viscous losses in the fluid in the cavity, the height of the cavity should be at least twice the thickness of the viscous boundary layer in the fluid:

$$h > 2\sqrt{\frac{2\mu a}{\rho k_0 c}}; k_0 \approx 3.83.$$ [Eqn. 2]

Where $\mu$ is the viscosity of the fluid, $\rho$ is the density of the fluid, c is the speed of sound in the fluid and $k_0$ is the first root of the derivative of the first order Bessel function of the first kind which describes the shape of the lowest frequency radial mode pressure oscillation and is constant. Rearranging the above expression and substituting in standard values for density and viscosity;

$$\frac{h^2}{a}$$

should be greater than $1 \times 10^{-7}$ m when the fluid in the cavity is a gas and greater than $4 \times 10^{-10}$ m when the fluid in the cavity is a liquid. The height of the cavity of such a sensor is typically less than 8 mm, leading to a compact device. In addition to the obvious commercial benefits of a compact sensor, this also reduces the fluid volume in the device increasing the speed at which the sensor can respond to changes in fluid properties.

In the embodiment shown in FIG. 1, the first end wall 3 is defined by the lower surface of a disc 6. The sidewall is defined by a ring 7. The transmitter comprises a piezoelectric disc 8 attached to the disc 6. When an appropriate electrical drive is applied the transmitter is caused to vibrate in a direction substantially perpendicular to the plane of the cavity 2, thereby generating radial pressure oscillations within the fluid in the cavity. The disc 6 has a thinner central region and a thicker outer region which reduces the motion of the outer portion of the disc in operation, reducing the transmission of parasitic oscillations through the structure of the sensor to the receiver. The piezoelectric disc 8 is not required to be formed of a piezoelectric material, but may be formed of any electrically active material such as, for example, an electrostrictive or magnetostrictive material. As such, the term "piezoelectric disc" is intended to cover electrostrictive or magnetostrictive discs as well.

Figure 1B:
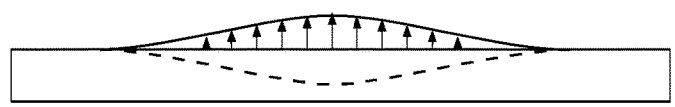

FIG. 1B shows a typical displacement profile of the first end wall of the cavity along a line bisecting the cavity. The solid curved line and arrows indicate the wall displacement at one point in time and the dashed curved line its displacement one half-cycle later. Note that the displacements as drawn in this figure and the other figures are exaggerated and the piezoelectric discs are omitted from the drawing for clarity.

Figure 1C:
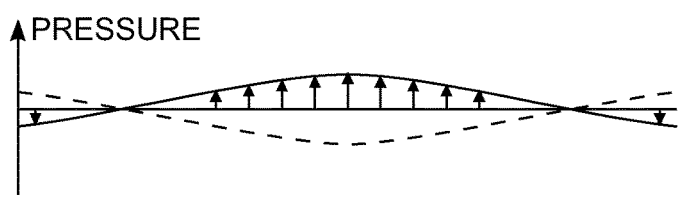

FIG. 1C shows a typical pressure oscillation profile for the cavity shown in FIG. 1A and FIG. 1B. The solid curved line and arrows indicate the pressure at one point in time, and the dashed curved line the pressure one half-cycle later. The radial dependence of this pressure oscillation p(r) approximates the form of the Bessel function:

$$p(r) = p_0 J_0\left(\frac{k_0 r}{a}\right); k_0 \approx 3.83.$$ [Eqn. 3]

Where $p_0$ is the maximum amplitude of the pressure oscillation, $J_0$ is the first order Bessel function of the first kind, $k_0$ is the first root of the derivative of that function, r is the radial position in the cavity and a is the radius of the cavity. In this case, the motion of the first end wall 3 and the pressure oscillation in the cavity show significant mode-shape matching. The embodiment disclosed in FIG. 1 shows an acoustic sensor wherein, in use, the lowest frequency, also known as lowest order or fundamental, mode of radial pressure oscillation is generated in the cavity. An acoustic sensor can be embodied wherein, in use, pressure oscillations with a radial mode possessing a resonant frequency higher than the fundamental mode are generated. These higher frequency oscillations are referred to as higher order radial modes of pressure oscillation in the cavity.

Figure 1D:
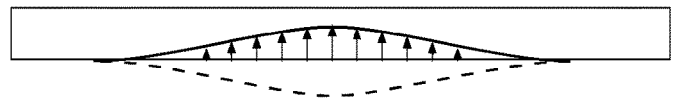

The pressure oscillation in the cavity shown in FIG. 1C drives a displacement in the second end wall 4. This displacement is shown in FIG. 1D. No phase relationship between the oscillations shown in FIGS. 1B, 1C and 1D should be inferred.

The receiver comprises a piezoelectric disc 9 attached to a disc 10. The displacement of the second end wall 4 causes an electrical signal to be generated by the piezoelectric disc 9. By comparison of the signal used to drive the transmitter and the signal generated by the receiver, properties of the fluid in the acoustic cavity can be determined such as the composition of a binary mixture of gases, temperature of a known fluid, density of a fluid or viscosity a fluid.

Figure 2:
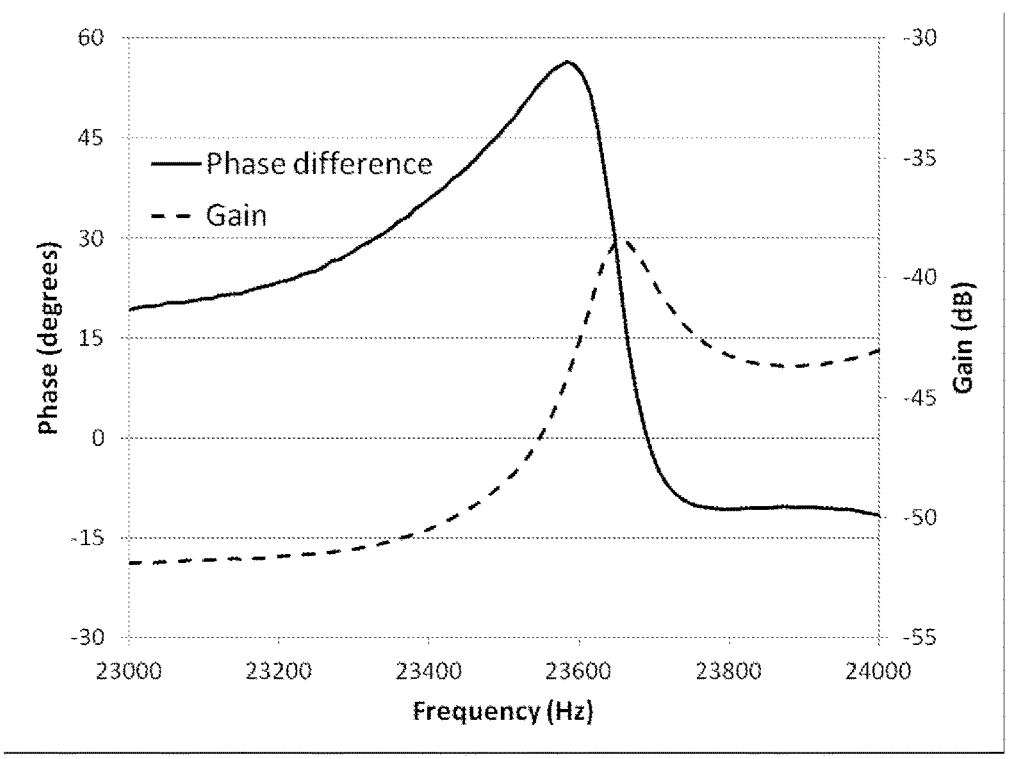
FIG. 2 shows typical phase difference and gain between transmitter and receiver in the vicinity of the cavity resonance for an embodiment of the acoustic sensor.

The acoustic sensor disclosed here can be used to measure the speed of sound in a fluid or a mixture of fluids. The resonant frequency of pressure oscillation $f_0$ disclosed in Equation 3 is described by the expression:

$$f_0 = \frac{k_0 c}{2\pi a}; k_0 \approx 3.83. \qquad [\text{Eqn. 4}]$$

Where $k_0$ is the first root of the derivative of the first order Bessel function of the first kind, c is the speed of sound in the cavity and a is the radius of the cavity. The resonant frequency of the pressure oscillation can be determined by observing the frequency at which the electrical amplitude gain between the transmitter and the receiver is maximised. One way to embody this would be to sweep the frequency of the electrical driving signal to the transmitter, recording the gain at each frequency. Similarly, the resonant frequency can be determined by comparing the phase of the input signal of the transmitter to the output signal of the receiver. One way to embody this would be to sweep the frequency of the drive signal and record the frequency at which the phase difference between the transmitter and the receiver is some constant value. FIG. 2 shows both the phase difference between transmitter and receiver and the electrical gain for an embodiment of the sensor described herein. One application enabled by accurate measurement of the speed of sound of a fluid is the determination of the composition of a binary mixture of gases. The equations to relate the composition of a binary gas to the speed of sound of a fluid are well known and are summarised in the prior art (EP 0813060).

The receiver and transmitter described above may also show resonant behaviour such that at certain frequencies the transmitter will show an enhanced displacement per volt of electrical drive signal and the receiver will generate an enhanced voltage for a given displacement. If any of these resonances were at a similar frequency to the resonance of the cavity, the signal of the sensor could be obscured. Therefore it is desirable that there are no resonances of the transmitter or the receiver that substantially overlap with the cavity. The resonant frequency of transmitters or receivers fabricated with piezoelectric discs mounted onto a substrate can be tuned by altering the thickness or stiffness of either the piezoelectric disc or the substrate. It is further desirable that the mechanical quality factor of the transmitter and the receiver are minimised, reducing the amplitude of any resonant behaviour. The quality factor of transmitters and receivers of the design described herein can be reduced by selected a piezoelectric disc formed from a material with a low mechanical quality factor. Preferably a piezoelectric material should be chosen with a low mechanical quality factor and a high magnitude piezoelectric coupling coefficient in the direction of poling ($d_{31}$).

To improve accuracy of these measurements, other properties of the fluid such as temperature, pressure and relative humidity may be measured. Means for measuring such properties could be integrated into the sensor disclosed here.

Figure 3A:
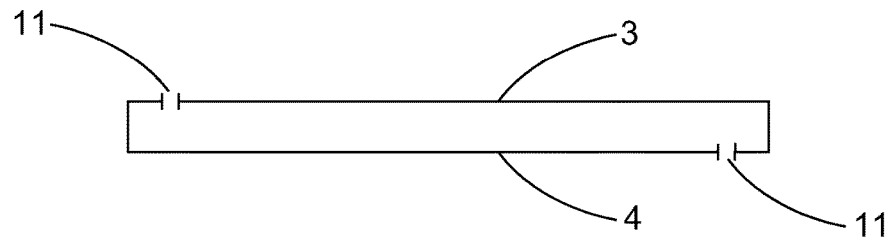
FIG. 3 shows the disposition of inlets and outlets to the cavity of several embodiments of the acoustic sensor.
Figure 3B:
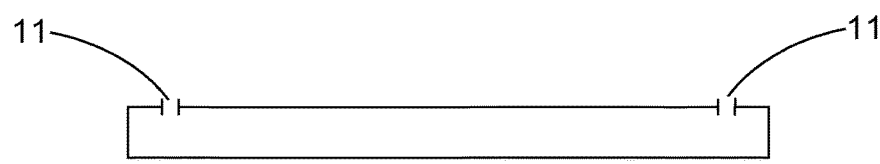
Figure 3C:
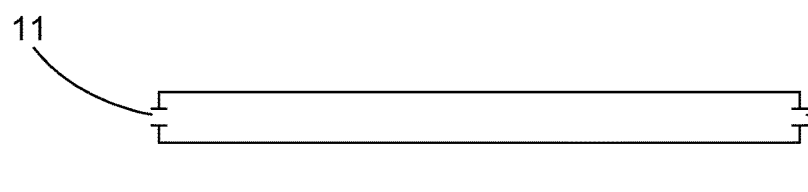
Figure 3D:
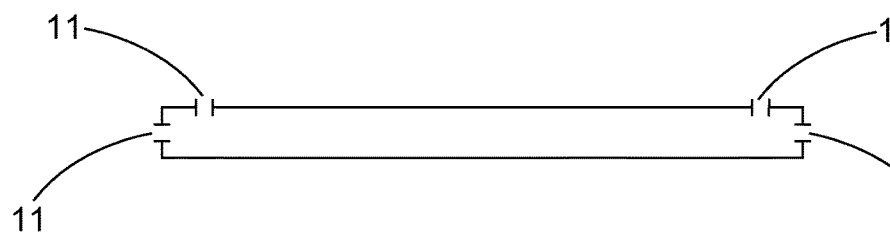
Figure 3E:
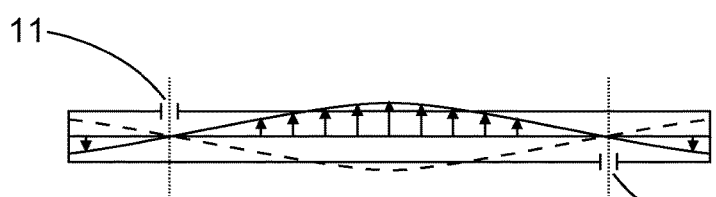

The cavity of the sensor disclosed herein is provided with one or more apertures which can be located at any position in the side walls or end walls of the cavity. In operation at least one of these apertures allows fluid to enter the cavity (inlet) and at least one of the apertures allows fluid to exit the cavity (outlet). In the embodiment shown in FIG. 3A the apertures 11 are located in opposing end walls 3, 4. In operation, the function of the inlet(s) and outlet(s) could be reversed or they could be apertures in the same end wall as shown in FIG. 3B. The apertures could be located in the sidewall, as shown in FIG. 3C, or in some combination of the sidewall and end wall, as shown in FIG. 3D. The role of the inlets and outlets is to allow flow of a test fluid through the cavity while causing minimal disruption to the pressure oscillation of the fluid in the cavity. To this end, it is most preferable for the inlets and outlets to be located at a nodal position of the pressure oscillation, as shown in FIG. 3E.

Figure 4A:
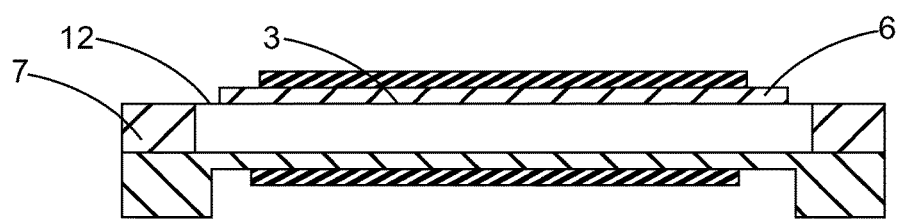
FIG. 4 shows embodiments of the acoustic sensor where one or more of the end walls of the resonant cavity are composed in part by a flexible membrane.
Figure 4B:
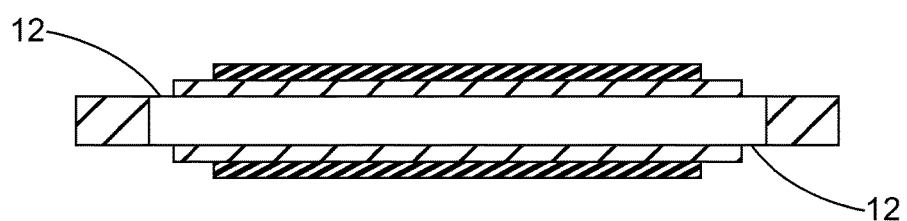

In the embodiment shown in FIG. 4A, the first end wall 3 is partly defined by the lower surface of a disc 6 attached to the ring 7 via a flexible membrane 12, this flexible membrane forming the remainder of the first end wall. An advantage of using this flexible membrane is improved mode shape matching between the transmitter and/or receiver motion and the pressure oscillation in the fluid. A second advantage is improved mechanical isolation between transmitter and the receiver, reducing the transmission of parasitic signals from the transmitter to the receiver through the structure of the device. FIG. 4B shows an embodiment where both of the end walls are partly defined by a flexible membrane.

The speed of sound in a fluid is dependent on temperature, so calibration of the sensor for temperature is important. Uncompensated changes in temperature change the speed of sound in the fluid in the cavity, masking other properties such as changing composition. Furthermore, a change in temperature can change the diameter of the cavity through thermal expansion, changing the resonant frequency of the cavity for a given fluid. It is known to compare the output of the sensor to that of a second sensor measuring the properties of a second 'reference' acoustic cavity either supplied with unmodified fluid or with a reference fluid sealed within it (for example: U.S. Pat. No. 3,848,457). Provided that the reference cavity and the 'test' cavity are within intimate thermal contact this technique could be used for temperature calibration in the present invention.

Figure 5A:
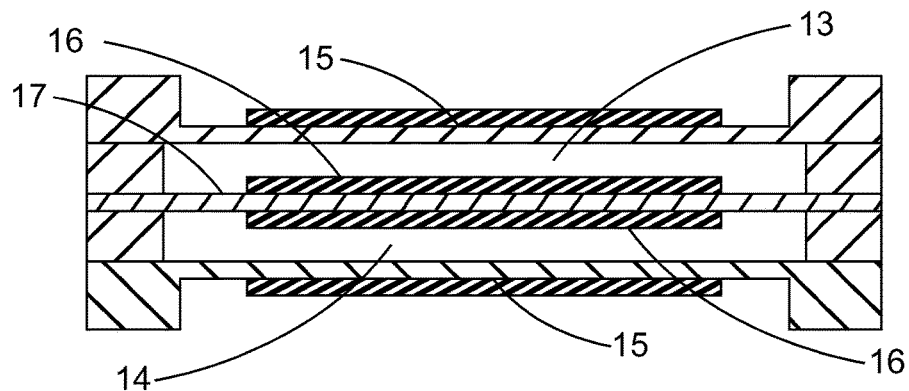
FIG. 5 shows embodiments of the acoustic sensor with two resonant acoustic cavities; a test cavity and a reference cavity.

In the embodiment shown in FIG. 5A the test acoustic cavity 13 is mounted directly above the reference acoustic cavity 14. Each cavity has a transmitter 15 consisting of a disc of piezoelectric material operatively associated with an end wall of the cavity. The second end wall of each cavity is formed by a disc of piezoelectric material 16 attached to a disc 17 which separates the two cavities. By measuring the resonant frequency of the reference acoustic cavity the temperature of the sensor can be measured, which can then be used to calibrate the data from the test cavity.

Figure 5B:
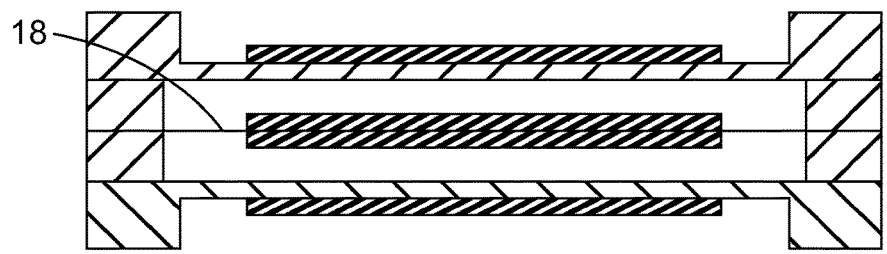
Figure 5C:
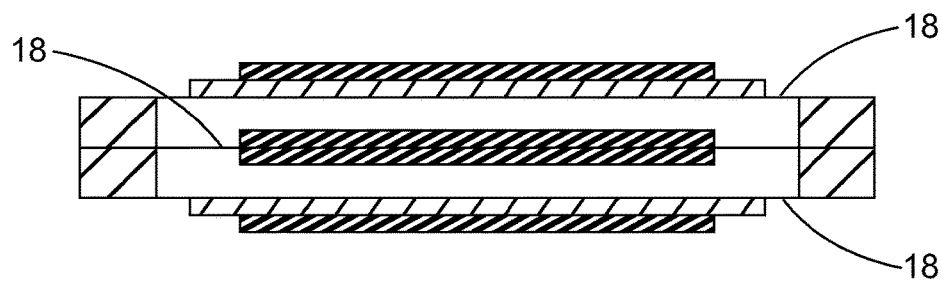
Figure 5D:
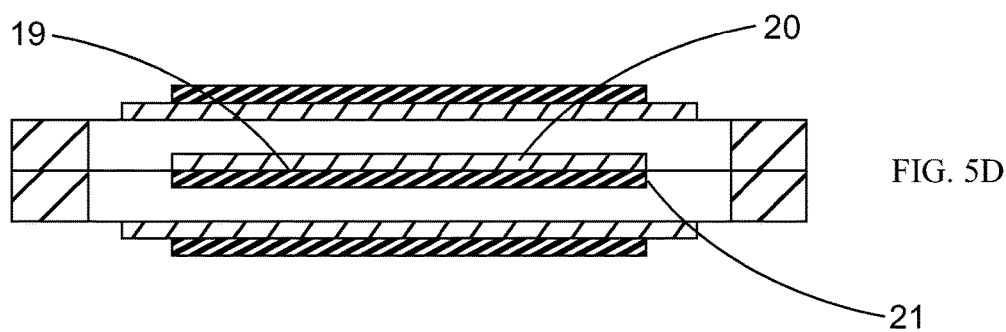

The embodiment shown in FIG. 5B replaces the disc separating the reference cavity and test cavity with a flexible membrane 18. This has the advantage of reducing parasitic signals travelling from transmitter to receiver through the structure of the device. In a preferred embodiment the membrane is manufactured from a foil of high thermal conductivity material leading to improved thermal conductivity between the reference cavity and the test cavity. In the embodiment shown in FIG. 5C the transmitter and receivers are also mounted on a flexible membrane 18. In the embodiment shown in FIG. 5D the receiver 19 is composed of a disc 20 operatively associated with a disc of piezoelectric material 21. The functions of the transmitter(s) and receiver(s) and the relative positions of the test and reference cavities shown in FIG. 5 could be reversed in additional embodiments.

Figure 6:
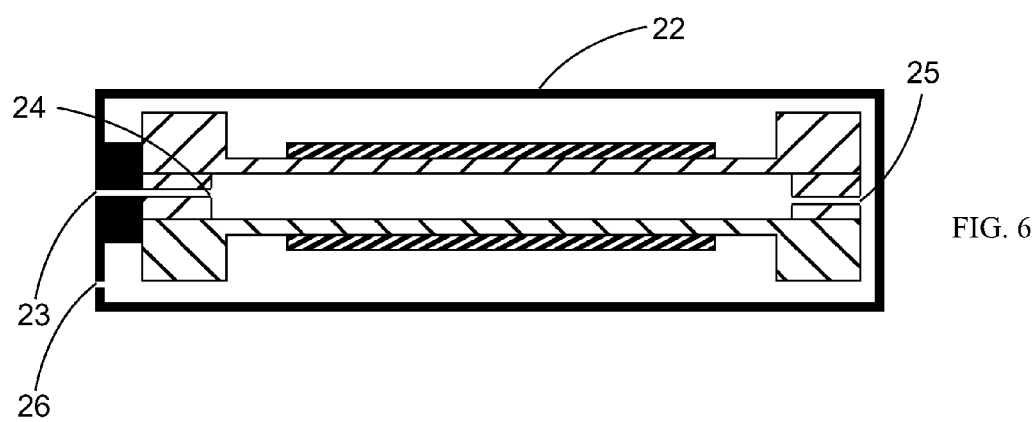
FIG. 6 shows an embodiment of the acoustic sensor enclosed within a casing such that pressure differences across the transmitter and the receiver are reduced.

The embodiment shown in FIG. 6 shows the resonant acoustic sensor within an enclosing casing 22. The casing has a fluid inlet 23 which is manifolded to the inlet of the sensor 24 in such a way as to create a pressure tight seal. The outlet of the sensor 25 is not manifolded to the outlet of the casing 26 such that fluid is free to pass into the volume between the sensor and the casing. This avoids large pressure differences between the test fluid and the fluid surrounding the sensor. This is preferable as it does not induce an additional force on the transmitter or the receiver avoiding distortion of the cavity volume (which may change the resonant frequency of the cavity) and stresses induced on the piezoelectric discs (which may change to the electrical characteristics of the transmitter or receiver).

Figure 7A:
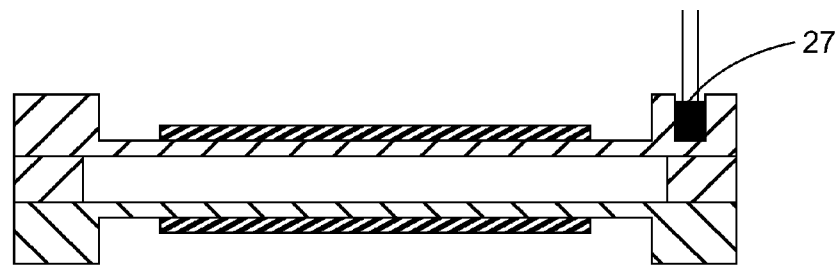
FIG. 7 shows embodiments of the acoustic sensor with an integrated thermometer and with a fluid path through the sensor designed to reduce the temperature difference between the fluid and the acoustic sensor.
Figure 7B:
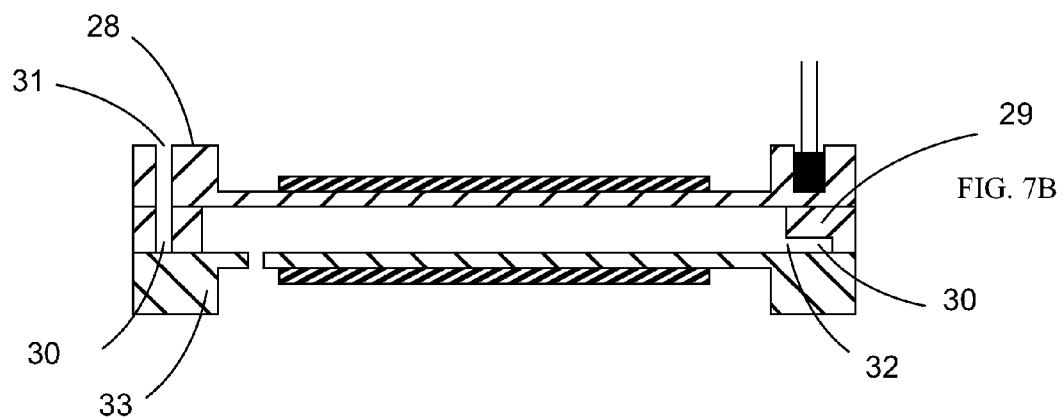

The embodiment shown in FIG. 7 shows an acoustic resonant sensor with an integrated temperature sensor 27 which may be a resistance thermometer, a thermocouple, a silicon bandgap temperature sensor, a thermistor or an infrared thermometer. In the embodiment shown in FIG. 7B the disc 28 forming the first end wall of the cavity and the ring 29 are further composed of a conduit 30 to transfer fluid from the sensor inlet 31 to the cavity inlet 32. The purpose of this conduit is to allow heat transfer between the fluid in the conduit, and the body of the sensor including the discs 28, 33 and the ring 29, thus allowing the fluid to reach a similar temperature to the body of the sensor. The conduit may have any number of paths through the material forming the discs 28, 33, the ring or any other material in good thermal contact with the body of the sensor. The length of the conduit should be such that the fluid can reach a temperature close to that of the sensor, this length will depend on the properties of the fluid (including thermal conductivity, density, viscosity and heat capacity), the properties of the material(s) forming the conduit (thermal conductivity, heat capacity) the flow rate of the fluid and the desired maximum temperature difference between the fluid and the cavity.

Figure 7C:
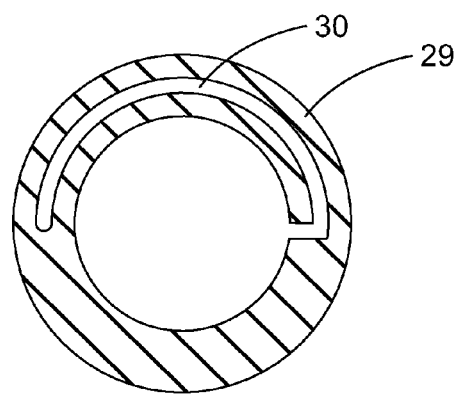

FIG. 7C shows the shape of the conduit 30 through the ring 29 in plan view. If the disc and cavity body are made of materials with a higher specific heat capacity than the fluid this will lead to slower changes in temperature of the fluid in the cavity (and disc) reducing the complexity of the temperature measurement. In a preferred embodiment the main body and disc are made of high thermal conductivity materials. In a more preferred embodiment the main body and disc are made of aluminium. Placing the thermometer in contact with the disc rather than the fluid itself has the further benefit for low thermal conductivity fluids such as gases that the thermometer is less sensitive to fluctuations in temperature from other sources such as heat conduction through any electrical connections to the thermometer. Avoiding direct contact between the fluid and the thermometer also has advantages when dealing with fluids that may corrode or damage a sensor, or fluids that may only contact approved materials to avoid contamination (e.g. for medical applications).

In a refinement to the design disclosed in FIG. 7, the thermometer 27 can be used to control a heater operatively associated with the material(s) forming some part of the end wall(s) or side wall of the acoustic cavity. This would allow thermostatic control of the cavity, making the temperature of the fluid in the cavity substantially independent of the temperature of the fluid arriving at the inlet to the sensor. This would allow more accurate calibration of the output of the sensor.

The invention claimed is:

1. An acoustic sensor comprising:
a side wall closed at each end by an end wall to form a cylindrical cavity which, in use, contains a fluid;
a transmitter operatively associated with a first of the end walls;
a receiver operatively associated with a second of the end walls;
wherein a radius, a, of the cavity and a height, h, of the cavity satisfies the following inequality: a/h is greater than 1.2;
wherein, in use, the transmitter causes axial oscillations of the first end wall in a longitudinal direction perpendicular to the plane of the end walls;
such that the axial oscillations of the first end wall drive radial oscillations of a pressure of a fluid in the cavity;
the radial oscillations in the pressure of the fluid drive axial oscillations of the second end wall associated with the receiver, generating an electrical signal; and
wherein, in use, the axial oscillations of the first end wall are mode-shape matched to the radial oscillations in the pressure of the fluid in the cavity.

2. An acoustic sensor according to claim 1, wherein a/h is greater than 2.

3. An acoustic sensor according to claim 1, wherein $h^2/a$ is greater than $4 \times 10^{-10}$ m.

4. An acoustic sensor according to claim 1, wherein the fluid in the cavity is a gas and wherein $h^2/a$ is greater than $1 \times 10^{-7}$ m.

5. An acoustic sensor according to claim 1, wherein, in use, a lowest resonant frequency of the radial oscillations of the pressure in the cavity is greater than 20 kHz.

6. An acoustic sensor according to claim 1 wherein, in use, the axial oscillations of the first end wall approximates the form of a Bessel function.

7. An acoustic sensor according to claim 1, wherein the transmitter or receiver is a piezoelectric device.

8. An acoustic sensor according to claim 7, wherein the transmitter or receiver includes a flexible membrane.

9. An acoustic sensor according to claim 1, wherein the radial oscillation in the fluid pressure of the cavity resonates based on an amplitude of an electrical signal used to drive the transmitter.

10. An acoustic sensor according to claim 1, wherein the radial oscillation in the fluid pressure of the cavity resonates based on a phase of an electrical signal used to drive the transmitter.

11. An acoustic sensor according to claim 1 arranged such that a resonance of at least one of the transmitter or the receiver does not overlap with a resonance of the cavity.

12. A sensor array comprising two or more acoustic sensors according to claim 1, wherein at least two sensor cavities are separated by a common end wall.

13. A sensor array comprising two or more acoustic sensors according to claim 1 wherein one or more of the sensors is arranged to allow calibration of one or more of the other sensors for factors including temperature, fluid pressure, thermal expansion or mechanical drift.

14. An acoustic sensor according to claim 1 wherein the sensor is enclosed in a casing.

15. An acoustic sensor according to claim 14 where a fluid inlet to the casing is manifolded to a fluid inlet of the sensor and a fluid outlet of the sensor outputs fluid into a volume between the sensor and the casing.

16. An acoustic sensor according to claim 1, further comprising a temperature sensor operatively associated with the side wall of the cavity.

17. An acoustic sensor according to claim 1, further comprising a conduit through the material of the first end wall or the second end wall of the sensor wherein, in use, the fluid flows through that conduit into the cavity.

18. An acoustic sensor according to claim 1, wherein the side wall or one or more of the end wall(s) are made from a material with thermal conductivity greater than 50 $wm^{-1}K^{-1}$.

* * * * *